(12) United States Patent
Van Vliet et al.

(10) Patent No.: US 9,089,098 B2
(45) Date of Patent: *Jul. 28, 2015

(54) METHOD FOR IDENTIFYING PLANT MATERIAL THAT SHOWS A REDUCED DISCOLOURATION, PLANTS THUS IDENTIFIED AND USE OF THE IDENTIFIED PLANTS FOR THE PRODUCTION OF COMMERCIAL CROP PLANTS SHOWING A REDUCED DISCOLOURATION

(75) Inventors: Willem Van Vliet, Maassluis (NL); Cornelis Maria Petrus Van Dun, Roosendaal (NL); Johannes Wilhelmus Schut, Wouw (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 493 days.

This patent is subject to a terminal disclaimer.

(21) Appl. No.: 12/631,385

(22) Filed: Dec. 4, 2009

(65) Prior Publication Data
US 2010/0175142 A1    Jul. 8, 2010

Related U.S. Application Data

(63) Continuation-in-part of application No. PCT/EP2008/005491, filed on Jul. 4, 2008.

(30) Foreign Application Priority Data

Jul. 6, 2007   (EP) .................................... 07075565

(51) Int. Cl.
| | | |
|---|---|---|
| *A01H 1/04* | (2006.01) | |
| *A01H 5/12* | (2006.01) | |
| *A01H 5/08* | (2006.01) | |

(52) U.S. Cl.
CPC .. *A01H 5/08* (2013.01); *A01H 1/04* (2013.01); *A01H 5/12* (2013.01)

(58) Field of Classification Search
None
See application file for complete search history.

(56) References Cited

U.S. PATENT DOCUMENTS

| | | | |
|---|---|---|---|
| 6,706,389 B1* | 3/2004 | Bates et al. | 428/349 |
| 6,784,344 B2* | 8/2004 | Olivas et al. | 800/305 |
| 8,809,631 B2* | 8/2014 | van Dun | 800/305 |
| 2005/0268360 A1 | 12/2005 | Gibson | |
| 2007/0180573 A1* | 8/2007 | van Dun | 800/278 |
| 2009/0053757 A1* | 2/2009 | Van Dun | 435/29 |
| 2013/0283405 A1* | 10/2013 | Van Vliet et al. | 800/260 |

FOREIGN PATENT DOCUMENTS

| | | |
|---|---|---|
| WO | WO 94/03607 | 2/1994 |
| WO | WO 2007/077229 | 7/2007 |
| WO | WO 2007/077231 | 7/2007 |

OTHER PUBLICATIONS

Saltveit et al, Postharvest Biology and Technology, 27 (2003) 277-283.*
Fabienne Brumiere, Inhibition of Enzymatic Browning in Food Products Using Bio-Ingredients, 2000, Thesis submitted to the Faculty of Graduate Studies and Research, Department of Food Science and Agricultural Chemistry, McGill University, Montreal, Quebec.*
Anderson and Morris, 2001, Crop Science, vol. 41, No. 6, pp. 1697-1705.*
Hisaminato et al, Biosci. Biotechnol. Biochem. 2001, vol. 65, No. 5, pp. 1016-1021, filed Dec. 4, 2009.*
Salveit et al. Lines of lettuce selected for ethylene insensitivity at the seedling stage displayed variable resposnes to ethylene or wounding as mature heads. Postharvest Biology and Technology. 2003. 27: 277-283.*
Castaner et al. Organic acids as browning inhibitors on harvested "Baby" lettuce and endive. Z Lebensm Unters Forsch A. 1997. 205: 375-379.*
Dogan et al. Characterization and purification of polyphenol oxidase from artichoke (*Cynara scolymus* L.). Journal of Agrciultral Food Chemistry. 2005. 53: 776-785.*
Campos-Vargas et al. Involvement of putative chemical wound signals in the induction of phenolic metabolism in wounded lettuce. Physiologia Plantarum. 2002. 114: 73-84.*
Hiromi Hisaminato, et al., Relationship Between the Enzymatic Browning and Phenylalanine Ammonia-lyase Activity of Cut Lettuce, and the Prevention of Browning by Inhibitors of Polyphenol Biosynthesis, Biosci. Biotechnol. Biochem. (2001) vol. 65, No. 5, p. 1016-1021.

(Continued)

*Primary Examiner* — Eileen B O Hara
*Assistant Examiner* — Ashley K Buran
(74) *Attorney, Agent, or Firm* — Vedder Price P.C.; Thomas J. Kowalski; Deborah L. Lu

(57) ABSTRACT

The invention relates to a method for testing a plant or plant part for exhibiting a reduced or absent wound-induced surface discoloration as compared to a control plant or plant part, which method comprises providing a plant or plant part that is obtained from a plant population that shows genetic variation, in particular a gene bank; optionally creating a wound surface on the plant or plant part; incubating the plant or plant part or the wound surfaces created thereon to allow for discoloration to occur therein or thereon; observing the discoloration in or on the plants or plant parts; comparing the observed discoloration with the discoloration that is observed in the control plant or plant part to assess whether the plant or plant part shows no discoloration or a discoloration that is reduced as compared to the control plant or plant part; and identifying a plant or plant part that shows no discoloration or a discoloration that is reduced as compared to the control plant or plant part as a plant that harbors the reduced wound-induced surface discoloration trait.

22 Claims, 5 Drawing Sheets

(56) References Cited

OTHER PUBLICATIONS

Staffan Muller-Wille, Early Mendelism and the Subversion of Taxonomy: Epistemological Obstacles as Institutions, Stud. Hist. Phil. Biol. & Biomed. Sci. (2005) vol. 36, p. 465-487.
Nils Roll-Hansen, Theory and Practice: The Impact of Mendelism on Agriculture, Life Sciences (2000) vol. 323 p. 1107-1116.
Larousse: Larousse Agricole, 1981 Librairie Larousse, 3012, 203514, p. 1022-1027, French.
Asakawa, M. et al., "Purification and Characterization of Polyphenoloxidase from Eggplant (Solanum melongena L.) cv. 'Chikuyo' Cultivated in Kumamoto," Natural Science, vol. 51, p. 105-115. (2002).
Demeke, T. et. al., "Effect of germination, seed abrasion and seed size on polyphenol oxidase assay activity in wheat," Plant Breeding 120, pp. 369-373. (2001).
Lopez-Galvez, G. et. al., "The visual quality of minimally processed lettuces stored in air or controlled atmosphere with emphasis on romaine and iceberg types," Postharvest Biology and Technology, vol. 8, pp. 179-190. 1996.
Uno, K, "Kinetic Study of Enzymatic Browning in Comestic and the North America Apple Pulps," Bulletin of Aichi Konan College, vol. 35, pp. 1-12. 2006.
Wehner et al "Vegetable Cultivar Descriptions for North America" Cucurbit Breeding Horticular Science, Mar. 20, 2007, pp. 1-13.

* cited by examiner

US 9,089,098 B2

METHOD FOR IDENTIFYING PLANT MATERIAL THAT SHOWS A REDUCED DISCOLOURATION, PLANTS THUS IDENTIFIED AND USE OF THE IDENTIFIED PLANTS FOR THE PRODUCTION OF COMMERCIAL CROP PLANTS SHOWING A REDUCED DISCOLOURATION

INCORPORATION BY REFERENCE

This application is a continuation-in-part application of International Patent Application Serial No. PCT/EP2008/005491 filed Jul. 4, 2008, which published as PCT Publication No. WO/2009/007066 on Jan. 15, 2009, which claims benefit of European Patent Application Serial No. 07075565.7 filed Jul. 6, 2007.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a method for identifying plant material for the presence therein of material that shows a reduced discoloration, in particular wound-induced surface discoloration, as compared to control plant material.

The invention further relates to plant material thus identified, to the use thereof in breeding and to plants obtained thereby.

BACKGROUND OF THE INVENTION

Harvesting and subsequent processing, packaging and storage of produce evokes a strong response of the plant material which in general leads to a fast reduction of the quality of the end product. Quality in this respect refers to several attributes, for example, color, taste, smell, and crispness, which is perceived by the consumer as freshness.

The response of produce towards processing may be of a combined physical, biochemical and physiological nature resulting in wilting, discoloration and senescence. In order to improve the quality of processed produce it will become increasingly important to develop plant varieties which show reduced levels of deterioration as a consequence of processing.

Lettuce is currently one of the fresh products that is increasingly offered to the consumer in a processed (e.g., cut, washed, packaged) form. This ready-to-eat product contributes to the convenience of the consumer and allows the development of new products like mixes of different leafy or other types of vegetables.

The most important problem that occurs during lettuce processing and storage is the wound surface discoloration. This disorder manifests as a pink or brown coloration at the wound surface of the cut leaves. The mid rib sections are especially prone to a strong staining in this respect. This negative quality trait is the most important trait to be controlled during processing, as packaged lettuce with a pink or brown discoloration is perceived by the consumer as a deteriorated product.

Although post-harvest treatments, for example, packaging under a controlled atmosphere, typically prevent discoloration and have improved the quality of fresh cut, packaged lettuce, a genetic solution is preferred. The reasons are that despite these treatments, a substantial part of the product is still lost due to causes such as damaged packages. Also shelf life after opening the package by the end user is typically very short, and, importantly, there is significant cost involved.

Therefore, breeding for lettuce plants that have improved processing traits, in particular reduced surface discoloration, is important for the lettuce processing industry. The same applies to the processing of other plant material, such as witloof and eggplant.

It is thus the object of the invention to enable the fast and efficient identification of plant material that has a reduced surface discoloration for use thereof in the production of crop plants that are less prone to post-harvest deterioration.

Citation or identification of any document in this application is not an admission that such document is available as prior art to the present invention.

SUMMARY OF THE INVENTION

The wound-induced discoloration process is a means of a plant to defend itself against damage via wound surfaces caused by pathogens, pests or physical factors (e.g., wind, rain, drought, cold, heat, etc.). It is therefore expected that natural variation for wound-induced discoloration is absent due to natural selection. Plants that are not able to defend themselves against external threats are weaker and have therefore less chances of surviving such threats.

Nevertheless, it was surprisingly found according to the invention that gene bank material contains significant variation in discoloration, in particular wound-induced discoloration. The inventors were able to demonstrate this by using a method for testing a plant or plant part for exhibiting a reduced or absent discoloration as compared to a control plant or plant part, which method comprises
 a) providing a plant or plant part that is obtained from a plant population that shows genetic variation, in particular a gene bank;
 b) optionally creating a wound surface on the plant or plant part;
 c) incubating the plant or plant part or the wound surfaces created thereon to allow for discoloration to occur therein or thereon;
 d) observing the discoloration in or on the plants or plant parts;
 e) comparing the observed discoloration with the discoloration that is observed in the control plant or plant part to assess whether the plant or plant part shows no discoloration or a discoloration that is reduced as compared to the control plant or plant part; and
 f) identifying a plant or plant part that shows no discoloration or a discoloration that is reduced as compared to the control plant or plant part as a plant that harbors the reduced wound-induced surface discoloration trait.

In this method, the discoloration is the result of the conversion of an endogenous substrate. Such discoloration will arise spontaneously upon incubation of the plant or plant part in a certain environment for a certain amount of time. The discoloration in this case is wound-induced. The invention particularly relates to the naturally occurring enzymatic pinking and browning reactions. The method of the invention is intended to identify plants that do not show this reaction or show a reduced reaction as compared to a control.

Alternatively, variation in discoloration may be detected by using a method for testing a plant or plant part for exhibiting a reduced or absent discoloration as compared to a control plant or plant part, which method comprises:
  a) providing a plant or plant part that is obtained from a plant population that shows genetic variation, in particular a gene bank;
  b) incubating the plant or plant part with a substrate that may be converted into a colored pigment to allow for discoloration to occur therein or thereon;
  c) observing the discoloration in or on the plants or plant parts;
  d) comparing the observed discoloration with the discoloration that is observed in the control plant or plant part to assess whether the plant or plant part shows no discoloration or a discoloration that is reduced as compared to the control plant or plant part; and
  e) identifying a plant or plant part that shows no discoloration or a discoloration that is reduced as compared to the control plant or plant part as a plant that harbors the reduced discoloration trait.

In the second method the discoloration is caused by the conversion of an exogenously added substrate that may be converted into a colored substrate that becomes visible when the reaction in the plant occurs. Such color reaction may or may not be wound-induced. It also occurs, for example, in the seeds coats of intact seeds. The screening method of the invention is intended to identify plants that do not show this reaction or show a reduced reaction as compared to a control.

Once suitable plant material harboring the reduced discoloration trait, in particular the reduced wound-induced surface discoloration trait, has been identified with one of these methods, such plant material is used according to the invention for introducing the trait into commercial crops. Such improved crop plants are also part of this invention.

The present invention is thus based on the use of a specific source of plant material that is tested. Cultured material does not show much variation with respect to discoloration. Unexpectedly, it was found that to the contrary germ plasm found in gene banks, such as accessions, do have significant variation in discoloration, in particular wound-surface induced surface discoloration. An accession is one specimen of a species, with a given locality. Accessions are for example stored in gene banks or libraries.

In one embodiment of this invention, the discoloration assays described above are used as an efficient tool to screen for naturally occurring genetic variants in crop species. The invention is in particular useful for testing lettuce germ plasm, for example from the species *Lactuca sativa* as well as related species like *Lactuca seriola, Lactuca virosa* etc.

The invention may also be used for, but is not limited to, crops that are cultivated for leaf or stem parts (endive, witloof), root or stem tubers (potato, sweet potato, celeriac), fruit parts (eggplant, apple, banana, avocado, peach, pear, apricot, mango), flowers or flower parts (artichoke, gerbera, chrysanthemum) and mushrooms.

Other assays which detect discoloration, in particular wound-induced surface discoloration of lettuce may be used as well in this respect, including but not limited to visual assessments of processed lettuce in different maturity stages.

By using such assays, accessions of different *Lactuca* species have been identified which contain significant variation in wound-induced surface discoloration, in particular of the leaves. The individual plants identified by the method described by this invention which have a reduced or absent wound-induced discoloration are used in breeding in order to develop lettuce plants which are improved with respect to their postharvest processing characteristics, especially with respect to wound surface discoloration. Such varieties are especially useful for the convenience market.

In addition, screening of a set of gene bank accessions of eggplant revealed accessions with reduced discoloration. The use of these accessions in the development of eggplants with reduced discoloration is also part of this invention.

The invention further relates to the use of plants that are identified via the method of the invention as the source of the reduced wound-induced surface discoloration trait. This source may be used as the parent in a conventional cross or as the donor of genetic material that underlies this trait.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially" of and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

Well 1: negative control (buffer only), well 2-6: 4 mM L-DOPA, well 3-6: in addition 0.1, 1.0, 5.0 and 10 mM L-cysteine, respectively.

Figure 6:
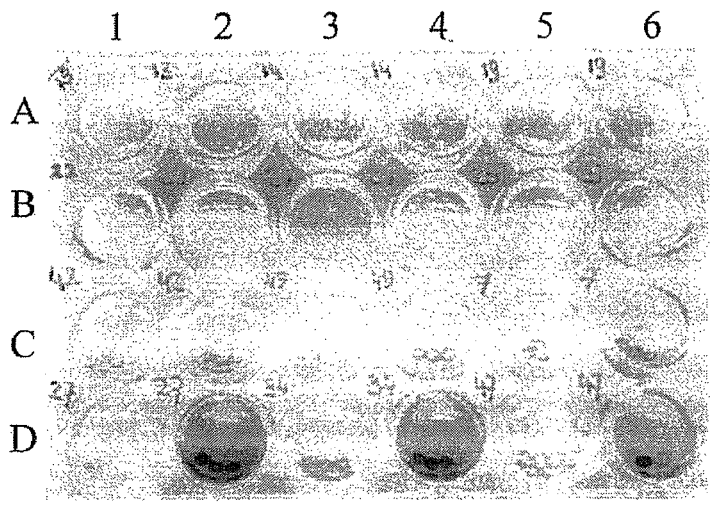
Figure 6:
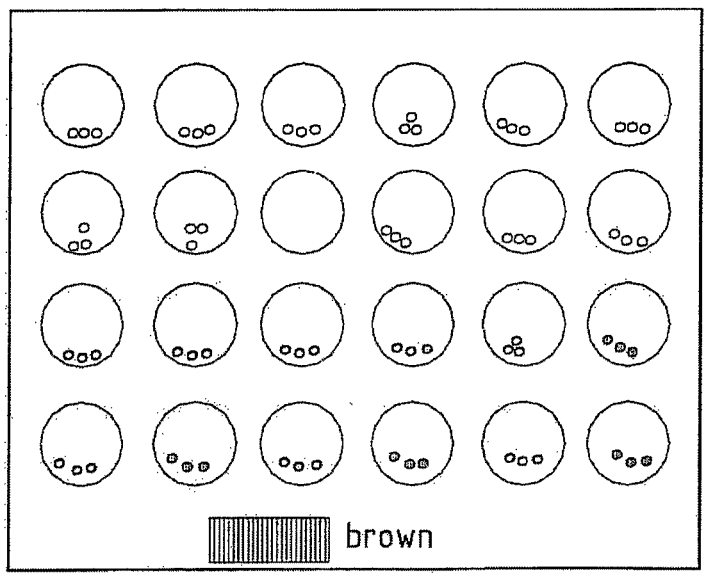

FIG. 6: Screening of genetic material of eggplant for variation in seed-associated PPO activity on the basis of incubation of seeds with the PPO substrate L-DOPA. The wells of columns 2, 4 and 6 contain 4 mM L-DOPA whereas the columns 1, 3 and 5 contain buffer only. Different genetic material in the form of eggplant seeds is assayed in this plate. Each batch of seeds is analysed side by side with and without L-DOPA at the positions A1 and A2, A3 and A4, A5 and A6, B1 and B2, B3 and B4, B5 and B6, C1 and C2, C3 and C4, C5 and C6, D1 and D2, D3 and D4, D5 and D6. The batches at position C5 and C6, D1 and D2, D3 and D4, D5 and D6 show the highest seed-associated PPO activity.

DETAILED DESCRIPTION OF THE INVENTION

Development of plants, and ultimately plant varieties, with a reduced wound surface discoloration through breeding initially requires the identification of genetic variants for this trait. This invention is concerned with this initial identification step and with the further step of introducing the trait into commercial crop plants. Once this first parent plant providing the desired trait has been identified, the development of plant varieties is then a matter of routine for the skilled breeder.

Wound-induced surface discoloration is a specific response of a plant upon cutting or other mechanical disturbances aimed at healing of the wound and defence against pathogenic invasion.

A wound response is a complex biological response of a plant to physical injury, which manifests both locally as well as systemically. The local response is mainly aimed at closing the wound surface which is effectuated by the local death of cells at or just behind the cut surface. Lignification or suberisation at the wound surface may be observed in many plant species which leads to an effective new insulation barrier between the plant body and the environment.

In addition to these visible effects, other responses like increased respiration or ethylene production are known to be induced. At the biochemical level studies have shown that wounding may lead to the induction of the phenylpropanoid pathway which is required for inter alia the production of polyphenols or lignins.

The key enzyme for this pathway is phenylalanine ammonia lyase (PAL), which is enhanced upon wounding by the induction of gene expression of at least one of the PAL isoforms. This response leads to the formation of polyphenols which are oxidised by polyphenol oxidase (PPO). PPO is residing in the plastids and is released and activated upon wounding. Oxidation of polyphenols leads to the formation of the highly reactive quinones. These quinones may react with amino acids or proteins, which leads to pink, brown or sometimes even black discoloration.

In lettuce, this response may be observed as well. When cut lettuce leaves are stored in a plastic bag in air the cut surface starts to develop a pinkish component at the wound surfaces which gradually turn brown after prolonged storage. Detailed biochemical analysis has shown that this response requires de novo synthesis of polyphenols, which are subsequently oxidised leading to a cascade of reactions, which may be observed as a pink or brown coloration at the wound surface.

The postharvest treatments which have been developed and which are currently applied by the lettuce processing industry counteract this particular response. The present invention provides a genetic method to counter this particular response, which may be applied to reduce or eliminate postharvest treatments aimed at wound-induced discoloration.

In order to allow development of crops with improved processing characteristics, a method is used according to the invention, which allows efficient detection of the surface discoloration that is diagnostic for postharvest discoloration of wounded cut crop plants, for example, lettuce.

These methods have been described in co-pending applications PCT/EP2007/000226 and PCT/EP2007/000230.

In one embodiment, leaf discs of lettuce plants are taken and incubated between wetted filter papers. Upon incubation, a pink discoloration will develop which is diagnostic for wound-induced pinking and browning of processed lettuce. Such method therefore allows a very efficient screening of populations of lettuce in which genetic variability resides in order to determine the presence of genetic variants which have a reduced wound surface discoloration and thereby improved processing quality.

Upon successful identification of such individual plants they may be used for breeding improved lettuce plants and ultimately develop lettuce varieties that are particularly useful for processing.

In order to identify plants with the reduced wound-induced surface discoloration trait natural genetic variation is exploited. Natural genetic variation is the variation in the DNA primary structure which occurs within the germplasm of such species and which is the result of errors during the replication and their maintenance within the DNA of the germinal cells.

The occurrence of such genetic polymorphisms within a population is determined by the fitness of the spontaneous mutation in a given genetic background as well as the selection imposed by the environment.

For lettuce this natural variation is present in the species *Lactuca sativa* but also in other *Lactuca* species such as *Lactuca serriola*, *Lactuca saligna* or *Lactuca virosa*. Plants identified according to the invention may thus also be identified in these species and be used for producing lettuce plants that harbor the reduced wound-induced surface discoloration. The underlying reason is that the natural, interspecific crossing barrier is not absolute and may, if necessary, be overcome by technologies known to the person skilled in the art such as embryo rescue.

Natural variation occurs in the plant material residing at breeding companies or institutes as gene banks in the form of seeds. In order to determine the presence of variants with a reduced wound surface discoloration, the plant material is raised under normal conditions for example in a greenhouse or in a field. At the young plant stage one may take samples, for example leaf discs, from the individual plants and determine the extent of discoloration using one of the methods described before. This approach for identifying lettuce or other crop plants, which are reduced with respect to their wound induced discoloration, is by far more efficient as opposed to a method in which the crop is grown to a mature stage, harvested, processed and assessed for processing quality.

In addition, wild relatives of the cultivated lettuce may develop in a completely different manner, which makes a comparative analysis less obvious. As it was found that the leaf disc response, which manifests as a pink surface discoloration, is diagnostic for the post-harvest discoloration, the method of the present invention may identify plants at an early developmental stage on the basis of a biochemical reaction, which may be used to improve the post-harvest characteristics of lettuce or other crops.

This approach allows an easier and more reliable comparison of different plant types. It was surprisingly found that within the *Lactuca* genus significant variation for wound induced discoloration may be observed.

The lettuce plants with a reduced level or absence of wound-induced discoloration, which have been found according to the invention, may be used in a regular breeding program to develop varieties tailored to the requirements of the processing industry. In such a breeding program breeders may use regular, well-known breeding methods like QTL-mapping, marker-assisted selection, and back-crossing, to combine the reduced level of wound-induced discoloration with other desired characteristics of cultivated lettuce, like The invention further relates to a method for producing plants with reduced wound-pathogen and pest resistance, absence or bolting and tipburn, etc. induced surface discoloration, comprising the steps of:
a) crossing a first parent plant with reduced wound-induced surface discoloration with a second parent plant to obtain F1 seed;
b) growing F1 plants from the F1 seeds and self-fertilising the F1 plants to obtain F2-seed;
c) selecting F2 plants for levels of wound-induced surface discoloration that are lower than the levels of at least the second parent plant as plants harboring the reduced wound-induced surface discoloration trait. These plants and their progeny that retains the reduced wound-induced surface discoloration trait are plants of the invention.

In one embodiment of the invention, the second parent plant is a cultured parent plant having agronomically acceptable characteristics, in particular lettuce.

In one embodiment the first parent is selected from the plants listed in Table 2. The second parent may be any lettuce, for example, a cultivated lettuce such as the iceberg lettuce Silvinas RZ.

The trait that is called herein "reduced wound-induced surface discoloration trait" is present in a plant when the score in the pinking test described in Example 1 is less than 3, preferably less than 2, more preferably 1.

It is now shown that variation is found in naturally occurring populations but it may also be induced by mutagenesis. This creates the possibility to combine different sources of variation to create an unprecedentedly low level of wound-induced discoloration. The combination of different sources of reduced wound-induced variation may be performed by crossing them, resulting into one or more hybrid seeds. If a hybrid plant from one of those seeds is showing a more reduced wound-induced discoloration, it may be used directly in practice.

In any case, a hybrid plant may be self-fertilised to obtain an F2-population. This F2-population may be used to test for allelism, i.e. both sources provide alleles reduced discoloration on the same locus. In the absence of allelism it is possible to find F2-individuals with a normal, high level, as well as F2-individuals with a more reduced level of wound surface discoloration than both parents. The latter F2-plants carry a combination of alleles for reduced discoloration from both parents and can be used for further breeding.

The process of combining alleles for reduced discoloration may be supported by molecular markers, like AFLPs, SFPs, etc. Additional assays to distinguish different levels of reduced discoloration, like visual assessment of stored, cut leaves of mature plants, may be used to identify the plants with the high reductions in wound surface discoloration resulting from combined alleles from different sources.

The invention will now be further described by way of the following non-limiting examples.

EXAMPLE 1

Screening of *Lactuca* Populations for Reduced Wound Surface Discoloration

Accessions of lettuce were screened for their potential to display wound induced discoloration. Seeds were germinated in trays containing potting soil in a greenhouse using standard conditions to grow lettuce. Young plants which had developed 3-4 true leaves were sampled using a cork borer. The leaf discs thus obtained were incubated between wetted filter papers in a container at 6° C. After about one week the pink discoloration was scored on a scale from 1 to 5 in which 1 means no detectable pink discoloration and 5 means very clear, maximum level of pink discoloration. The result is shown in Table 1. This table shows the internal reference and their respective score. Accessions that were confirmed to have a reduced pink discoloration are identified below.

Figure 1:
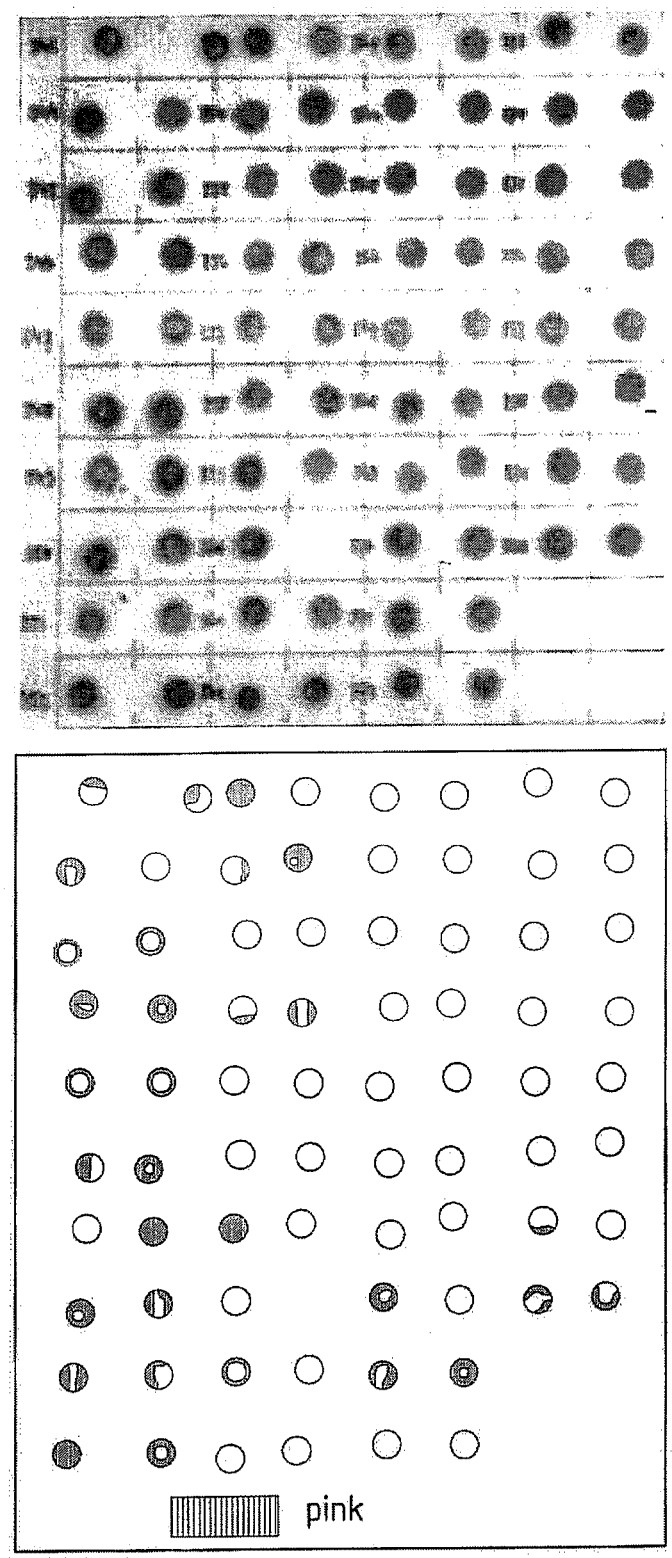
FIG. 1: Leaf disc pinking assay of *Lactuca* accessions. Variability of the response which manifests as different degrees of pink disclouration is observed between the accessions.

An example of the observed differences in the pinking reaction of different accessions using the pinking leaf disc assay is shown in FIG. 1.

Surprisingly, it was found that several accessions showed reduced discoloration. This was unexpected, because this trait is considered a disadvantage under natural and grower's conditions as the process resulting in discoloration is considered to protect the plant against adverse biotic and abiotic stress factors entering through a wounded spot. The most interesting accessions from this test were resown and retested according to the same protocol as mentioned above. Reduced pinking was confirmed for number 651968 (*L. virosa;* plot nr. 366, NCIMB 41489). Additional accessions were tested according to the same protocol as mentioned above and retested for confirmation. Reduced pinking was found and confirmed for number 650147 (*L. saligna;* NCIMB 41485). The accessions that were found to show reduced wound-induced surface discoloration are listed in Table 2.

Well-known accessions such as 'Iceberg' and 'Salinas' were not showing any signs of reduced pinking in this test.

TABLE 2

Overview of accessions with reduced discoloration of wound surfaces.

| Number | species | type | accession number |
|---|---|---|---|
| 651968 | *L. virosa* | | NCIMB 41489 |
| 650147 | *L. saligna* | | NCIMB 41485 |
| 07V.67586 | *L. sativa* | crisphead | NCIMB 41569 |

Seeds of the numbers 651968, 650147 and 07V.67586 were deposited with NCIMB Ltd, Ferguson Building, Craibstone Estate, Bucksburn, Aberdeen, Scotland, AB21 9YA, UK.

Table 1

Pinking score of different *Lactuca* accessions. Each field number refers to an individual accession. Two plants per accession were sampled. The score indicates the level of pinking: 1=no pinking to 5=strong pinking. In case the two plants differed in pinking two scores are indicated. In case one score is indicated the two plants reacted identical in the test.

| Veld nr. | Score |
|---|---|
| 1 | 5 |
| 2 | 3 |
| 3 | 3 |
| 4 | 3 |

-continued

| Veld nr. | Score |
|---|---|
| 5 | 5 |
| 6 | 5 |
| 7 | 5 |
| 8 | 4 |
| 9 | 4 |
| 10 | 4 |
| 11 | 3 |
| 12 | 4 |
| 13 | 5 |
| 14 | 5 |
| 15 | 5 |
| 16 | 5 |
| 17 | 3 |
| 18 | 5 |
| 19 | 5 |
| 20 | 5 |
| 21 | 2 |
| 154 | 5 |
| 155 | 5 |
| 156 | 5 |
| 157 | 5 |
| 158 | 5 |
| 159 | 4 |
| 160 | 5 |
| 161 | 5 |
| 162 | 5 |
| 163 | 5 |
| 164 | 4 |
| 165 | 5 |
| 166 | 5 |
| 167 | 5 |
| 168 | 5 |
| 169 | 5 |
| 170 | 5 |
| 171 | 5 |
| 172 | 5 |
| 173 | 5 |
| 174 | 5 |
| 175 | 5 |
| 176 | 4 |
| 177 | 2 |
| 178 | 5 |
| 179 | 2 |
| 180 | 5 |
| 181 | 5 |
| 182 | 5 |
| 183 | 5 |
| 184 | 3 |
| 185 | 5 |
| 186 | 5 |
| 187 | 5 |
| 188 | 5 |
| 189 | 5 |
| 190 | 5 |
| 191 | 5 |
| 192 | 5 |
| 193 | 5 |
| 194 | 5 |
| 195 | 5 en 4 |
| 196 | 5 |
| 197 | 5 |
| 198 | 5 |
| 199 | 5 |
| 200 | 5 |
| 201 | 5 |
| 202 | 5 |
| 203 | 5 |
| 204 | 5 |
| 205 | 5 |
| 206 | 5 |
| 207 | 5 |
| 208 | 5 |
| 209 | 5 |
| 210 | 5 |
| 211 | 5 |
| 212 | 5 |
| 213 | 5 |

-continued

| Veld nr. | Score |
|---|---|
| 214 | 5 |
| 215 | 5 |
| 216 | 5 |
| 217 | 5 |
| 218 | 5 |
| 219 | plant nog to klein |
| 220 | 4 |
| 221 | 4 |
| 222 | 4 |
| 223 | 4 |
| 224 | 3 en 4 |
| 225 | 4 |
| 226 | 4 |
| 227 | 4 |
| 228 | 5 |
| 229 | 5 |
| 230 | 5 |
| 231 | 4 |
| 232 | 4 |
| 233 | 4 |
| 234 | 4 |
| 235 | 4 |
| 236 | 2 en 4 |
| 237 | 2 |
| 238 | 4 |
| 239 | 4 |
| 240 | 4 |
| 241 | 4 |
| 242 | 4 |
| 243 | 4 |
| 244 | 5 |
| 245 | 5 |
| 246 | 5 |
| 247 | 3 en 4 |
| 248 | 4 |
| 249 | 5 |
| 250 | 4 |
| 251 | 4 |
| 252 | 4 |
| 253 | 4 |
| 254 | 4 |
| 255 | 4 |
| 256 | 4 |
| 257 | 4 |
| 258 | 4 |
| 259 | 5 |
| 260 | 5 |
| 261 | 4 |
| 262 | 4 |
| 263 | 4 |
| 264 | 4 |
| 265 | 4 |
| 266 | 4 |
| 267 | 5 |
| 268 | 4 |
| 269 | 4 |
| 270 | 4 |
| 271 | 5 |
| 272 | 5 |
| 273 | 5 |
| 274 | 5 |
| 275 | 5 |
| 276 | 1 en 3 |
| 277 | 2 en 5 |
| 278 | 1 en 4 |
| 279 | 5 |
| 280 | 5 |
| 281 | 5 |
| 282 | 5 |
| 283 | 5 |
| 284 | 3 |
| 285 | 5 |
| 286 | 5 |
| 287 | 3 en 5 |
| 288 | 5 |
| 289 | 5 |

| Veld nr. | Score |
| --- | --- |
| 290 | 5 |
| 291 | 3 en 5 |
| 292 | 5 |
| 293 | 5 |
| 294 | 5 |
| 295 | 5 |
| 296 | 5 |
| 297 | 5 en 4 |
| 298 | 2 en 4 |
| 299 | 4 |
| 300 | 2 en 3 |
| 301 | 4 |
| 302 | 4 |
| 303 | 4 |
| 304 | 5 |
| 305 | 5 |
| 306 | 5 |
| 307 | 5 |
| 308 | 5 |
| 309 | 5 |
| 310 | 5 |
| 311 | 5 |
| 312 | 5 |
| 313 | 2 en 5 |
| 314 | 3 en 5 |
| 315 | 5 |
| 316 | 5 |
| 317 | 5 en 3 |
| 318 | 5 |
| 319 | 4 |
| 320 | 5 |
| 321 | 5 en 2 |
| 322 | 5 en 2 |
| 323 | 2 en 1 |
| 324 | 4 en 3 |
| 325 | 5 |
| 326 | 5 |
| 327 | 4 |
| 328 | 2 |
| 329 | 2 en 3 |
| 330 | 1 |
| 331 | 2 |
| 332 | 3 |
| 333 | 2 en 3 en 5 |
| 334 | 5 |
| 335 | 5 |
| 336 | 5 |
| 337 | 3 |
| 338 | 5 |
| 339 | 4 |
| 340 | 5 |
| 341 | 3 |
| 342 | 2 en 1 |
| 343 | 4 |
| 344 | 5 |
| 345 | 5 |
| 346 | 5 |
| 347 | 4 |
| 348 | 5 |
| 349 | 5 |
| 350 | 5 |
| 351 | 5 |
| 352 | 5 |
| 353 | 4 |
| 354 | 5 |
| 355 | 4 |
| 356 | 5 |
| 357 | 4 |
| 358 | 4 |
| 359 | 3 |
| 360 | 4 |
| 361 | 4 |
| 362 | 4 |
| 363 | 3 |
| 364 | 3 |
| 365 | 3 |
| 366 | 2 |
| 367 | 2 |
| 368 | 3 |
| 369 | 2 |
| 370 | 4 |
| 371 | 4 |
| 372 | 3 |
| 373 | 3 en 2 |
| 374 | 3 |
| 375 | 4 |
| 376 | 5 |
| 377 | 5 |
| 378 | 5 |
| 379 | 5 |
| 380 | 5 |

EXAMPLE 2

Field Screening

Figure 2:
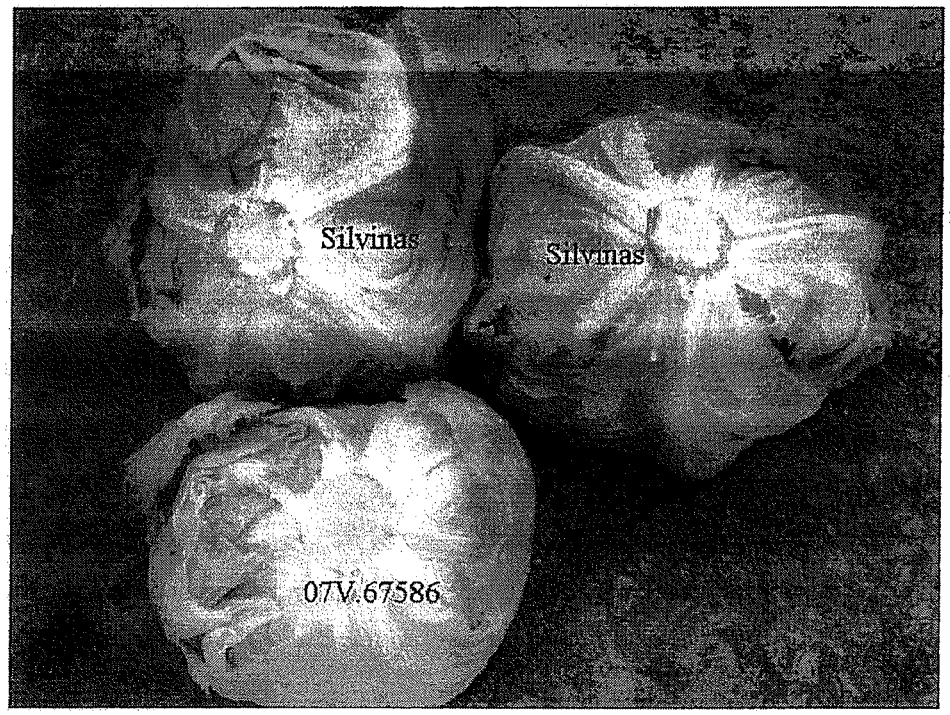
FIG. 2: Pictures of iceberg lettuce heads of number 07V.67586 with reduced discoloration and cv. 'Silvinas' with normal discoloration.
Figure 2:
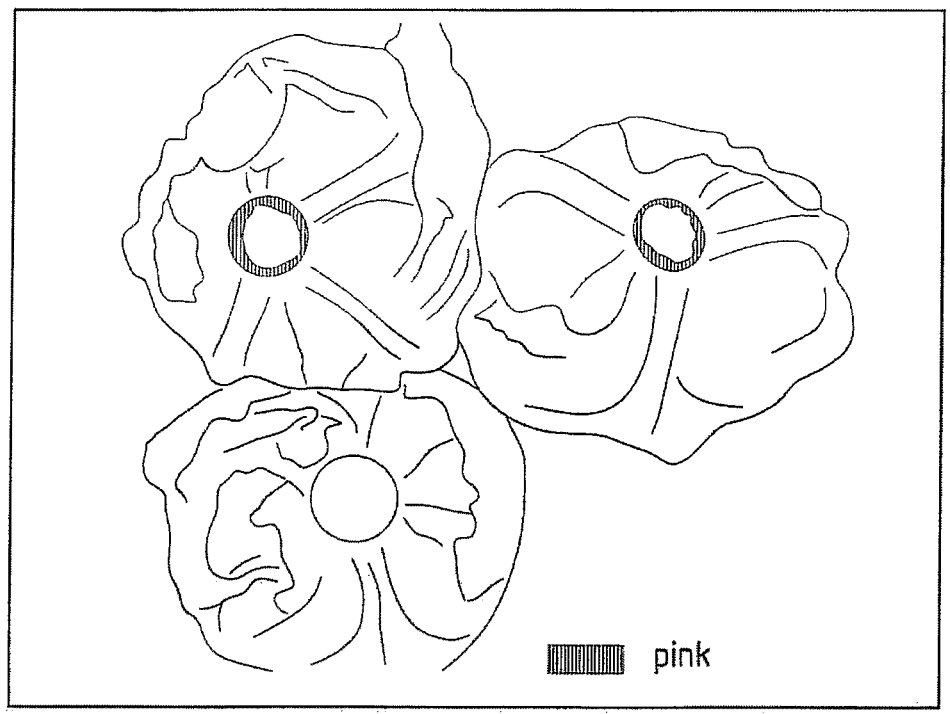

A field screening was performed by visual assessment of cut crisphead lettuce heads. In one accession reduced discoloration of wound-surfaces was observed (FIG. 2). This accession has number 07V.67586. It was re-tested by visual assessment in a following field trial and was confirmed to have reduced discoloration. This visual assessment was done one day after cutting. Surprisingly a follow-up test according to the protocol mentioned in Example 1 did not show reduced pinking. This could be an indication for a different genetic cause of reduced discoloration in number 07V.67586 than in the other accessions described in Example 1.

EXAMPLE 3

Reduced Discoloration in Eggplant

Figure 3:
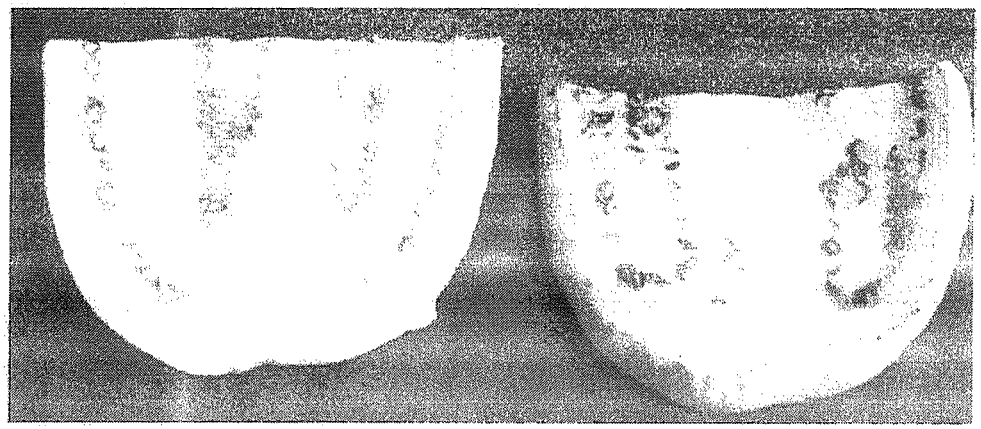
FIG. 3: Browning response of fresh cut eggplant. On the left fruit tissue is shown a few hours after cutting stored at room temperature. On the right fruit tissue is shown which has been incubated for 24 hours at room temperature. The seed browning may clearly be observed.
Figure 3:
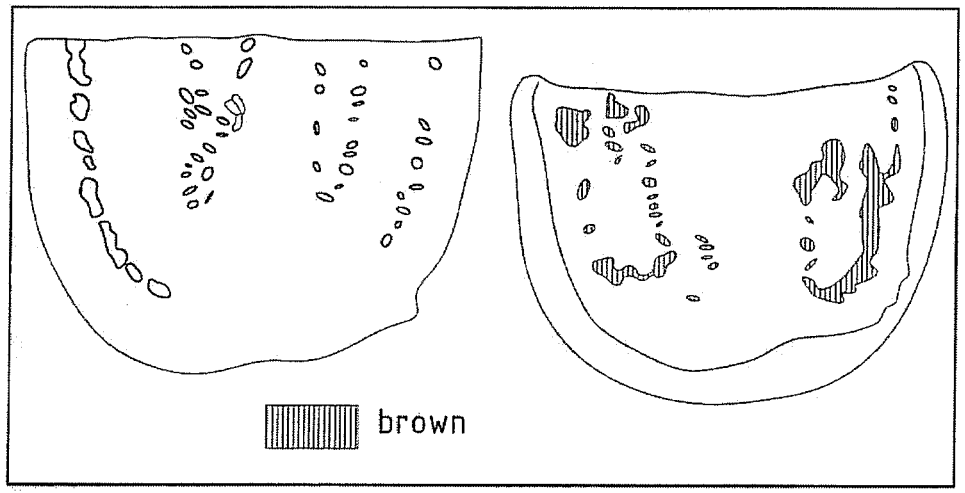

Upon cutting and packaging of eggplant fruits a rapid browning reaction may be observed. The wound surface of the cut fruit tissue rapidly turns brown which reduces the quality of the product. More importantly the seeds embedded within the fruit flesh show a strong brown discoloration which stands out against the background as shown in FIG. 3.

For industrial use of fresh cut eggplant or the use of eggplant as fresh produce, seed browning needs to be prevented. In order to determine the biochemical nature of the brown discoloration of cut eggplant fruits, the browning reaction was observed both with and without L-cysteine which is a strong inhibitor of polyphenol oxidase (PPO). The result of this analysis is shown in FIG. 4.

Figure 4:
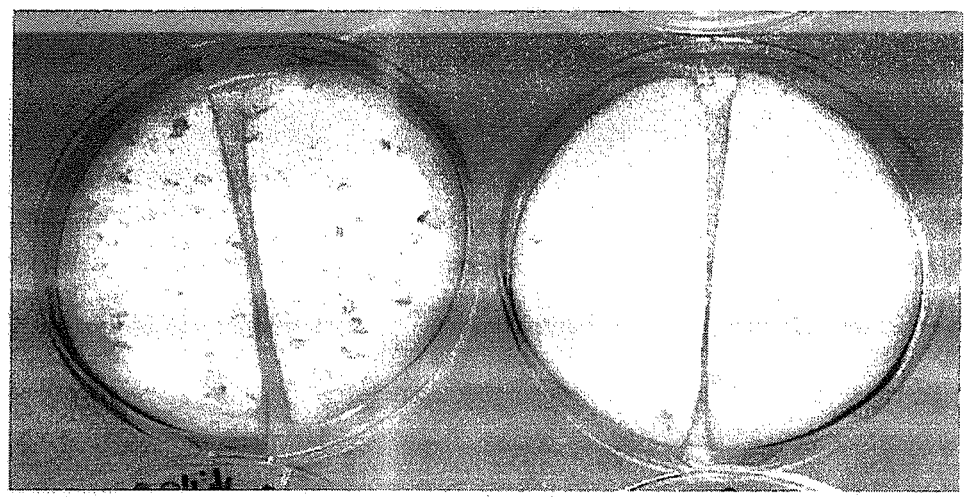
FIG. 4: Cut slices of eggplant and the browning response. On the left two half slices have been incubated at room temperature for 24 hours in 50 mM mes buffer pH=5.5. On the right the half slices have been incubated under the same condition but with added 10 mM L-cysteine.
Figure 4:
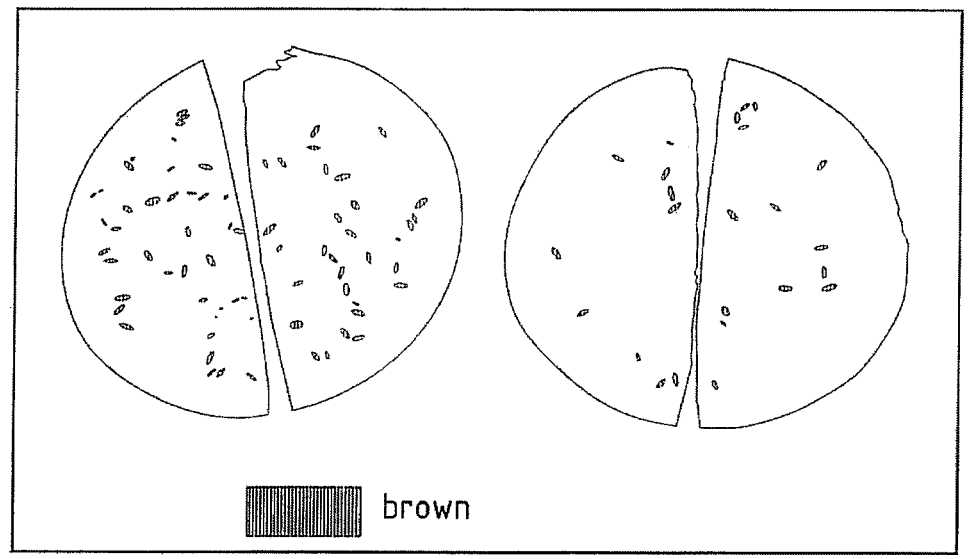

The result shown in FIG. 4 demonstrates that the browning reaction may be inhibited by the exogenously supplied PPO inhibitor L-cysteine. Therefore, the browning response is clearly PPO-mediated.

In order to prevent the brown discoloration in eggplant caused by the seeds using a genetic approach, genetic material was screened for variation in seed-associated PPO activity. For that purpose the method was used that relies on the conversion of a substrate, such as L-DOPA, into a colored pigment, such as melanin.

Figure 5:
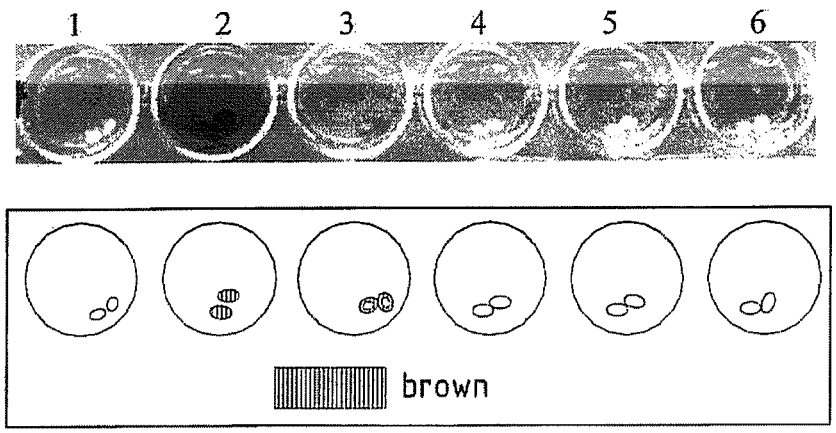
FIG. 5: Black discoloration of eggplant seeds upon incubation of the seeds in a solution containing 4 mM L-DOPA.

Upon incubation of eggplant seeds in a solution containing dihydroxyphenylalanine (L-DOPA) as a PPO substrate, melanin formation clearly visible as a black discoloration occurs. This black discoloration is PPO-mediated because it may be completely inhibited by L-cysteine which is shown in FIG. 5.

The L-DOPA mediated seed discoloration of eggplant is used to identify genetic material which has reduced seed-associated PPO activity. This screening resulted in the identification of genetic material which shows a significant reduction of the seed-associated PPO activity. The result of such screening is illustrated in FIG. 6.

The eggplant material which has been taken through this screening method and which has shown a strong reduction in seed-associated PPO activity is summarised in Table 3.

In this screening some breeding lines show a considerable reduction in seed-associated PPO activity (13, 14, 42, 49), whereas others show strong browning (7, 27, 34, 47).

TABLE 3

| Number | Breeding line/code | Reduced PPO activity |
|---|---|---|
| 13 | AB5480 | + |
| 14 | AB5701 | + |
| 19 | 05N.1130-1 | + |
| 22 | SNL.109 | + |
| 24 | 06N.1268-1 | + |
| 25 | SNL.111 | + |
| 42 | AB5028 | + |
| 49 | AB5103 | + |
| 7 | AB5261 | − |
| 27 | 06N.244-2 | − |
| 34 | AB5007 | − |
| 47 | AB5101 | − |

By making crosses between two lines which show this reduction in seed-associated PPO activity, hybrids are obtained that are more suited for both industrial as fresh market use. Furthermore, wild accessions have been found that are either closely related to eggplant (19) or more distantly related (22, 24, 25) and which show a very strong reduction in seed-associated PPO activity. These accessions are used as a start of a backcross program which results in breeding lines and hybrids that are even more suitable for both industrial as fresh market purpose. In the backcross process, the method of screening mentioned above is used to assist in selection for the strongest reduction in seed-associated PPO activity.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

Each patent, patent application, and publication cited or described in the present application is hereby incorporated by reference in its entirety as if each individual patent, patent application, or publication was specifically and individually indicated to be incorporated by reference.

What is claimed is:

1. A method for selecting a leafy vegetable plant that exhibits a reduced or absent physical wound-induced surface discoloration at harvest as compared to a control plant, wherein the plant belongs to the *Asteraceae* family, wherein the control plant is a plant of which a part of a leaf or midrib tissue when incubated between two sheets of wetted filter paper for 7 days at 5° C. shows pink discoloration around the edges, the method comprising:

sampling a part of the leafy vegetable plant at a developmental stage different than harvest, said sampling comprising:
physically wounding a surface of a part of the leafy vegetable plant, said part comprising a leaf or a midrib tissue or part thereof;
physically wounding a surface of a part of the control plant, said part comprising a leaf or a midrib tissue or part thereof;
incubating aqueously the leaf or midrib tissue or part thereof of each of the leafy vegetable plant and the control plant to allow for discoloration to occur therein or thereon;
observing any discoloration in or on the leaf or midrib tissue or part thereof of the leafy vegetable plant and the control plant;
comparing any observed discoloration in or on the leaf or midrib tissue or part thereof of the leafy vegetable plant with discoloration that is observed in the control leaf or midrib tissue;
identifying the leaf or midrib tissue or part thereof of the leafy vegetable plant part that shows no discoloration or a discoloration that is reduced as compared to the control leaf or midrib tissue; and
selecting the leafy vegetable plant of the identified leafy vegetable plant leaf or midrib tissue or part thereof as the leafy vegetable plant that has the reduced wound-induced surface discoloration trait;
wherein the leafy vegetable plant exhibits a reduced or absent wound-induced surface discoloration at harvest.

2. The method of claim 1, wherein the plant is selected from the group consisting of:
lettuce, endive and witloof.

3. The method of claim 1, wherein the leaf or midrib tissue or part thereof comprises a leaf disc or disc from midrib tissue.

4. The method of claim 1, wherein the incubating aqueously comprises incubating: in a solution, or in water, or on or between filter paper, or in a solution and on or between filter paper, or in water and on or between filter paper.

5. The method of claim 4, wherein the solution contains L-3,4-dihydroxyphenylalanine, chlorogenic acid, isochlorogenic acid, L-tyrosine or catechol.

6. The method of claim 4, wherein the leafy vegetable plant is
a lettuce and the solution contains tyrosine, caffeic acid, or a chlorogenic acid derivative.

7. The method of claim 1, wherein the incubating includes incubating the leaf or midrib tissue or part thereof with a substrate that may convert into a colored pigment that allows discoloration to occur in or on the leaf or midrib tissue or part thereof.

8. The method of claim 7, wherein the substrate comprises 3,4-dihydroxyphenylalanine (DOPA), 3,4-dihydroxy benzoic acid, 3,4-dihydroxyphenylethylamine (dopamine), 4-methyl catechol, adrenaline, caffeic acid, caffeylamide, catechin, catechol, chlorogenic acid, chlorogenic acid derivatives, cinnamic acid derivatives, coumaric acid, dopamine-HC1, epicatechin, flavonols, flavonol glycosides, gallic acid, isochlorogenic acid, leucocyanidin, leucodelphinidin, m-cresol, noradrenaline, p-coumaric acid, p-coumaric acid derivatives, p-cresol, p-hydroxyphenyl, p-hydroxyphenyl pyruvic acid, propionic acid, pyrogallol, or tyrosine.

9. The method of claim 8, wherein the substrate is L-DOPA.

10. The method of claim 7, wherein the leaf or midrib tissue or part thereof comprises a leaf disc.

11. The method of claim 1 further comprising growing said leafy vegetable plant to maturity; crossing the selected leafy vegetable plant with a second parent plant to obtain F1 seed; growing F1 plants from the F1 seeds and self-fertilising the F1 plants to obtain F2 seed; and selecting plants from the F2 seed having the reduced wound-induced surface discoloration trait.

12. The method of claim 7, wherein the discoloration may be inhibited or reversed by L-cysteine.

13. The method of claim 1, wherein the leafy vegetable plant belongs to the genus *Lactuca*.

14. The method of claim 1, wherein the leafy vegetable plant belongs to the species *Lactuca sativa*.

15. The method of claim 1 wherein the leafy vegetable plant belongs to the genus *Cichorium*.

16. The method of claim 1 wherein the leafy vegetable plant belongs to the species *Cichorium intybus*.

17. The method of claim 1 wherein the leafy vegetable plant belongs to the species *Cichorium endivia*.

18. The method of claim 11, wherein the leafy vegetable plant belongs to the genus *Lactuca*.

19. The method of claim 11, wherein the leafy vegetable plant belongs to the species *Lactuca sativa*.

20. The method of claim 11 wherein the leafy vegetable plant belongs to the genus *Cichorium*.

21. The method of claim 11 wherein the leafy vegetable plant belongs to the species *Cichorium intybus*.

22. The method of claim 11 wherein the leafy vegetable plant belongs to the species *Cichorium endivia*.

* * * * *